United States Patent [19]
Hektner

[11] Patent Number: 6,019,718
[45] Date of Patent: Feb. 1, 2000

[54] APPARATUS FOR INTRAVASCULAR RADIOACTIVE TREATMENT

[75] Inventor: Thomas R. Hektner, Medina, Minn.

[73] Assignee: SciMed Life Systems, Inc., Maple Grove, Minn.

[21] Appl. No.: 08/866,560

[22] Filed: May 30, 1997

[51] Int. Cl.[7] .................................................. A61N 5/00
[52] U.S. Cl. ............................................................. 600/3
[58] Field of Search ............................................. 600/1–7

[56]  References Cited

U.S. PATENT DOCUMENTS

| 2,546,761 | 3/1951 | Loftus | 128/1.2 |
|---|---|---|---|
| 2,862,108 | 11/1958 | Meilink | 250/106 |

(List continued on next page.)

FOREIGN PATENT DOCUMENTS

| 2166915 | 8/1996 | Canada . |
|---|---|---|
| 0 433 011 B1 | 6/1991 | European Pat. Off. . |
| 0 497 495 A2 | 8/1992 | European Pat. Off. . |
| 0 514 913 A2 | 11/1992 | European Pat. Off. . |
| 0 593 136 A1 | 4/1994 | European Pat. Off. . |
| 0 633 041 A1 | 1/1995 | European Pat. Off. . |
| 0 686 342 A1 | 12/1995 | European Pat. Off. . |
| 0 688 580 A1 | 12/1995 | European Pat. Off. . |
| 0 696 906 B1 | 2/1996 | European Pat. Off. . |
| 0 749 764 A1 | 12/1996 | European Pat. Off. . |
| 0 754 472 A2 | 1/1997 | European Pat. Off. . |
| 0 754 473 A2 | 1/1997 | European Pat. Off. . |
| 0 778 051 A1 | 6/1997 | European Pat. Off. . |
| 0 801 961 A2 | 10/1997 | European Pat. Off. . |
| 0 813 894 A2 | 12/1997 | European Pat. Off. . |
| 0 629 380 B1 | 7/1998 | European Pat. Off. . |
| 9102312 U | 6/1992 | Germany . |
| 195 26 680 A1 | 1/1997 | Germany . |
| 197 24 223 C1 | 4/1997 | Germany . |
| 197 54 870 A1 | 8/1998 | Germany . |
| WO 86/03124 | 6/1986 | WIPO . |
| WO 93/04735 | 3/1993 | WIPO . |
| WO 94/25106 | 11/1994 | WIPO . |
| WO 94/26205 | 11/1994 | WIPO . |
| WO 95/07732 | 3/1995 | WIPO . |
| WO 95/19807 | 7/1995 | WIPO . |
| WO 95/26681 | 10/1995 | WIPO . |
| WO 96/06654 | 3/1996 | WIPO . |
| WO 96/10436 | 4/1996 | WIPO . |
| WO 96/13303 | 5/1996 | WIPO . |

(List continued on next page.)

OTHER PUBLICATIONS

Tjho–Heslinga et al. "Results of ruthenium irradiation of uveal melanoma", *Radiotherapy Oncology*, vol. 29, pp. 33–38, 1993.

Lommatzsch et al. "Radiation effects on the optic nerve observed after brachytherapy of choroidal melanomas with 106Ru/106Rh plaques", *Graefe's Arch. Clin. Exp. Ophthalmology*, vol. 232, pp. 482–487, 1994.

(List continued on next page.)

*Primary Examiner*—John P. Lacyk
*Attorney, Agent, or Firm*—Crompton, Seager & Tufte LLC.

[57] ABSTRACT

A device, system and method for delivering radiation to interior body sites, including stenosed blood vessel regions for the purpose of inhibiting restenosis after angioplasty. A string having a radioactive first region, a second region, and an intermediate region is disposed within or along an elongate shaft having a distal return member. The string intermediate portion is typically initially looped over the distal return member. The radioactive region is normally initially disposed within a radiation shielding vault or enclosure. The elongate shaft can be advanced within a vessel to the site to be treated, followed by pulling the string to advance the string radioactive region within the shaft to the treatment site. After exposure, the string can be retracted, placing the radioactive string region back within the vault. The string can be used and re-used without sterilization when used within catheter lumens not in fluid communication with bodily fluids.

17 Claims, 4 Drawing Sheets

U.S. PATENT DOCUMENTS

| | | | |
|---|---|---|---|
| 2,955,208 | 10/1960 | Stevens | 250/108 |
| 3,060,924 | 10/1962 | Rush | 128/1.2 |
| 3,147,383 | 9/1964 | Prest | 250/108 |
| 3,324,847 | 6/1967 | Zoumboulis | 128/1.2 |
| 3,505,991 | 4/1970 | Hellerstein et al. | 128/1.1 |
| 3,643,096 | 2/1972 | Jeffries Jr. et al. | 250/108 R |
| 3,669,093 | 6/1972 | Sauerwein et al. | 128/1.1 |
| 3,750,653 | 8/1973 | Simon | 128/1.2 |
| 3,811,426 | 5/1974 | Culver et al. | 128/1.2 |
| 3,861,380 | 1/1975 | Chassagne et al. | 128/1.2 |
| 3,866,050 | 2/1975 | Whitfield | 250/497 |
| 3,927,325 | 12/1975 | Hungate et al. | 250/435 |
| 4,096,862 | 6/1978 | DeLuca | 128/348 |
| 4,220,864 | 9/1980 | Sauerwein et al. | 250/497 |
| 4,225,790 | 9/1980 | Parsons, Jr. et al. | 250/497 |
| 4,244,357 | 1/1981 | Morrison | 128/1.2 |
| 4,281,252 | 7/1981 | Parsons, Jr. et al. | 250/497 |
| 4,314,157 | 2/1982 | Gaines | 250/497 |
| 4,364,376 | 12/1982 | Bigham | 128/1.1 |
| 4,584,991 | 4/1986 | Tokita et al. | 128/1.1 |
| 4,588,395 | 5/1986 | Lemelson | 604/59 |
| 4,631,415 | 12/1986 | Sauerwein et al. | 250/497.1 |
| 4,702,228 | 10/1987 | Russell, Jr. et al. | 128/1.2 |
| 4,706,652 | 11/1987 | Horowitz | 128/1.2 |
| 4,763,642 | 8/1988 | Horowitz | 128/1.2 |
| 4,763,671 | 8/1988 | Goffinet | 128/786 |
| 4,782,834 | 11/1988 | Maguire et al. | 128/344 |
| 4,784,116 | 11/1988 | Russell, Jr. et al. | 128/1.2 |
| 4,799,479 | 1/1989 | Spears | 128/303.1 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,897,076 | 1/1990 | Puthawala et al. | 600/7 |
| 4,936,823 | 6/1990 | Colvin et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman et al. | 128/659 |
| 4,976,680 | 12/1990 | Hayman et al. | 600/7 |
| 4,976,690 | 12/1990 | Solar et al. | 604/96 |
| 5,030,194 | 7/1991 | Van't Hooft | 600/3 |
| 5,032,113 | 7/1991 | Burns | 604/96 |
| 5,059,166 | 10/1991 | Fischell et al. | 600/3 |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,103,395 | 4/1992 | Spako et al. | 364/413.26 |
| 5,106,360 | 4/1992 | Ishiwara et al. | 600/2 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 | 1/1993 | Fischell et al. | 600/3 |
| 5,183,455 | 2/1993 | Hayman et al. | 600/7 |
| 5,199,939 | 4/1993 | Dake et al. | 600/3 |
| 5,213,561 | 5/1993 | Weinstein et al. | 600/7 |
| 5,267,960 | 12/1993 | Hayman et al. | 604/106 |
| 5,282,781 | 2/1994 | Liprie | 600/3 |
| 5,302,168 | 4/1994 | Hess | 600/3 |
| 5,308,356 | 5/1994 | Blackshear Jr. et al. | 606/194 |
| 5,344,383 | 9/1994 | Liping | 600/3 |
| 5,354,257 | 10/1994 | Roubin et al. | 600/7 |
| 5,370,685 | 12/1994 | Stevens | 623/2 |
| 5,391,139 | 2/1995 | Edmundson | 600/7 |
| 5,405,309 | 4/1995 | Carden, Jr. | 600/3 |
| 5,409,015 | 4/1995 | Palermo | 128/772 |
| 5,411,466 | 5/1995 | Hess | 600/3 |
| 5,417,653 | 5/1995 | Sahota et al. | 604/20 |
| 5,425,720 | 6/1995 | Rogalsky et al. | 604/198 |
| 5,429,582 | 7/1995 | Williams | 600/2 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,532,122 | 7/1996 | Drukier | 435/5 |
| 5,538,494 | 7/1996 | Matsuda | 600/1 |
| 5,540,659 | 7/1996 | Teirstein | 604/104 |
| 5,545,132 | 8/1996 | Fagan et al. | 604/96 |
| 5,556,389 | 9/1996 | Liprie | 604/264 |
| 5,558,642 | 9/1996 | Schweich, Jr. et al. | 604/96 |
| 5,575,749 | 11/1996 | Liprie | 600/3 |
| 5,605,530 | 2/1997 | Fischell et al | 600/3 |
| 5,611,767 | 3/1997 | Williams | 600/2 |
| 5,616,114 | 4/1997 | Thornton et al. | 600/3 |
| 5,618,266 | 4/1997 | Liprie | 604/21 |
| 5,624,372 | 4/1997 | Liprie | 600/3 |
| 5,643,171 | 7/1997 | Bradshaw et al. | 600/1 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlein et al. | 600/3 |
| 5,683,345 | 11/1997 | Waksman et al. | 600/3 |
| 5,688,220 | 11/1997 | Verin et al. | 600/1 |
| 5,707,332 | 1/1998 | Weinberger | 600/3 |
| 5,720,717 | 2/1998 | D'Andrea | 604/21 |
| 5,722,984 | 3/1998 | Fischell et al. | 606/198 |
| 5,728,042 | 3/1998 | Schwager | 600/3 |
| 5,730,698 | 3/1998 | Fischell et al. | 600/3 |
| 5,782,740 | 7/1998 | Schneiderman | 600/1 |
| 5,782,742 | 7/1998 | Crocker et al. | 600/3 |
| 5,795,286 | 8/1998 | Fischell et al. | 600/3 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,816,259 | 10/1998 | Rose | 128/898 |
| 5,816,999 | 10/1998 | Bischoff et al. | 600/3 |
| 5,820,553 | 10/1998 | Hughes et al. | 600/426 |
| 5,833,593 | 11/1998 | Liprie | 600/3 |
| 5,840,008 | 11/1998 | Klein et al. | 600/3 |
| 5,840,009 | 11/1998 | Fischell et al. | 600/3 |
| 5,840,064 | 11/1998 | Liprie | 604/96 |
| 5,843,163 | 12/1998 | Wall | 623/1 |
| 5,851,171 | 12/1998 | Gasson | 600/3 |
| 5,851,172 | 12/1998 | Bueche et al. | 600/7 |
| 5,855,546 | 1/1999 | Hastings et al. | 600/3 |
| 5,857,956 | 1/1999 | Liprie | 600/7 |
| 5,863,284 | 1/1999 | Klein | 600/3 |
| 5,863,285 | 1/1999 | Coletti | 600/3 |
| 5,865,720 | 2/1999 | Hastings et al. | 600/3 |
| 5,871,436 | 2/1999 | Eury | 600/3 |
| 5,871,437 | 2/1999 | Alt | 600/3 |
| 5,873,811 | 2/1999 | Wang et al. | 600/5 |
| 5,879,282 | 3/1999 | Fischell et al. | 600/3 |
| 5,882,290 | 3/1999 | Kume | 600/3 |
| 5,882,291 | 3/1999 | Bradshaw et al. | 600/3 |
| 5,891,091 | 4/1999 | Teirstein | 604/104 |
| 5,897,573 | 4/1999 | Rosenthal et al. | 606/224 |
| 5,899,882 | 5/1999 | Waksman et al. | 604/96 |

FOREIGN PATENT DOCUMENTS

| | | |
|---|---|---|
| WO 96/14898 | 5/1996 | WIPO . |
| WO 96/17654 | 6/1996 | WIPO . |
| WO 96/22121 | 7/1996 | WIPO . |
| WO 96/29943 | 10/1996 | WIPO . |
| WO 96/40352 | 12/1996 | WIPO . |
| WO 97/07740 | 3/1997 | WIPO . |
| WO 97/18012 | 5/1997 | WIPO . |
| WO 97/09937 | 6/1997 | WIPO . |
| WO 97/19706 | 6/1997 | WIPO . |
| WO 97/25102 | 7/1997 | WIPO . |

| | | |
|---|---|---|
| WO 97/25103 | 7/1997 | WIPO . |
| WO 97/40889 | 11/1997 | WIPO . |
| WO 98/01183 | 1/1998 | WIPO . |
| WO 98/01184 | 1/1998 | WIPO . |
| WO 98/01185 | 1/1998 | WIPO . |
| WO 98/01186 | 1/1998 | WIPO . |
| WO 98/11936 | 3/1998 | WIPO . |
| WO 98/16151 | 4/1998 | WIPO . |
| WO 98/20935 | 5/1998 | WIPO . |
| WO 98/25674 | 6/1998 | WIPO . |
| WO 98/29049 | 7/1998 | WIPO . |
| WO 98/30273 | 7/1998 | WIPO . |
| WO 98/34681 | 8/1998 | WIPO . |
| WO 98/36788 | 8/1998 | WIPO . |
| WO 98/36790 | 8/1998 | WIPO . |
| WO 98/36796 | 8/1998 | WIPO . |
| WO 98/39052 | 9/1998 | WIPO . |
| WO 98/39062 | 9/1998 | WIPO . |
| WO 98/39063 | 9/1998 | WIPO . |
| WO 98/40032 | 9/1998 | WIPO . |
| WO 98/46309 | 10/1998 | WIPO . |
| WO 98/55179 | 12/1998 | WIPO . |
| WO 98/57706 | 12/1998 | WIPO . |
| WO 99/01179 | 1/1999 | WIPO . |
| WO 99/02219 | 1/1999 | WIPO . |
| WO 99/04706 | 2/1999 | WIPO . |
| WO 99/04856 | 2/1999 | WIPO . |
| WO 99/10045 | 3/1999 | WIPO . |

OTHER PUBLICATIONS

Nakayama et al., "Comparison of the Cytotoxicity of Different Hydroperoxides to V79 Cells", *Free Rad. Res. Comms.*, vol. 14 No. 3, pp. 173–178.

Varma et al., "Hydrogen Peroxide in Human Blood", *Free Rad. Res. Comms.*, vol. 14, No. 2, pp. 125–131.

Sutherland, "Managing Cancer Through Synergy", *Administrative Radiology Journal*, Nov. 1996 pp. 21–27.

*Radiotherapy of Intraocular and Orbital Tumors*, Springer–Verlak publishers, Berlin Heidelberg and New York, copyright 1993, pp. 23–30 and 363–367.

Magnussen, "Oxidizing Materials", College of Science, Texas A&M University, last revised Nov. 25, 1996, Copyright 1996 (http://joy.tarnu.edu/nanweb/oxidizers.html).

Raloff, "Nuclear Medicine Gets Friendlier—Experimental Therapies Seek to Poison Just the Disease", *Science News*, vol. 152, Jul. 19, 1997, pp. 40–41.

Fackelmann, "Harbinger of a Heart Attack—Does a Protein in the Blood Foretell Heart Trouble", *Science News*, vol. 151, Jun. 14, 1997, pp. 374–375.

"Aids and Cancer Cured by Hyper–Oxygenation", *Now What*, Issue No. 1, 1987, Waves Forest, Monterey, California.

Li et al., "Reactive Oxygen Species Induce Apoptosis of Vascular Smooth Muscle Cell", *FEBS Letters*, 404, 1997, pp. 249–252.

Kalli, "Oxygen Emulsion The Question of Free Radicals", Internet Address http://www.livelinks.com/sumeria/oxy/rad2.html, Aug. 1, 1997.

Barry, "Reactive Oxygen Species in Living Systems—Source: Biochemistry, and Role in Human Disease", Internet Address http://www.livelinks.com/sumeria/oxy/reactive.html, Jul. 21, 1997 from *American Journal of Medicine*, vol. 91, No. 3C, Sep. 30, 1991, p. 14S(9).

Block, "Peroxygen Compounds, Chapter 9", *Disinfection Sterilization, and Preservation* Fourth Edition, Lea & Febiger, Philadelphia, Copyright 1991.

Moore, "Free Radial Generation by Thyroid Peroxidase and Its Effects on Cells in Vitro", PhD. Dissertation Group in Endocrinology–University of California, Berkeley, California, Dec. 1990.

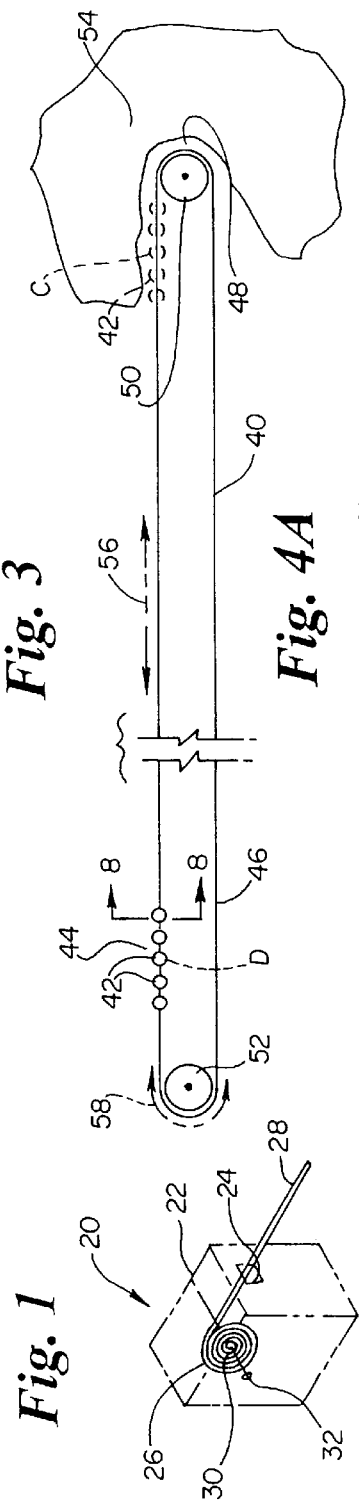
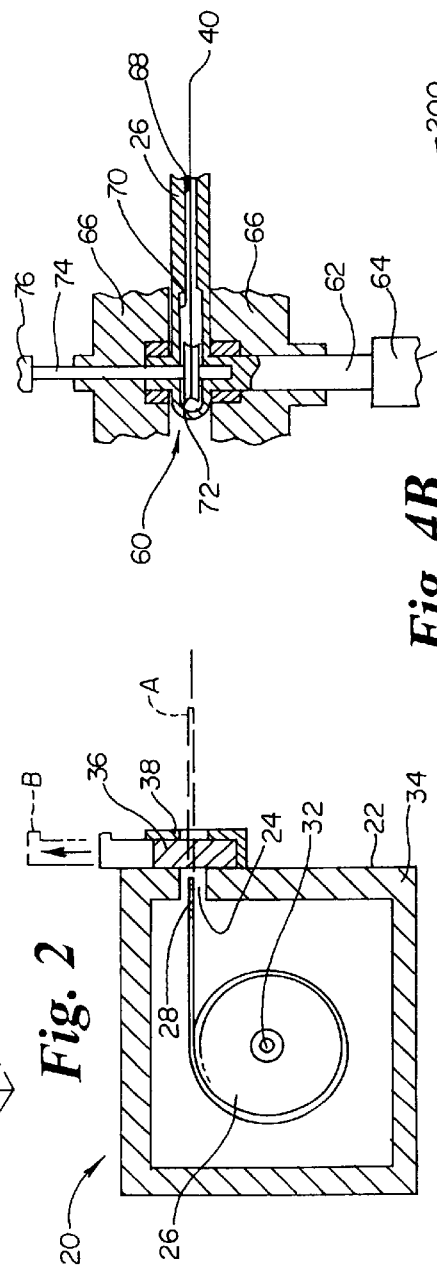
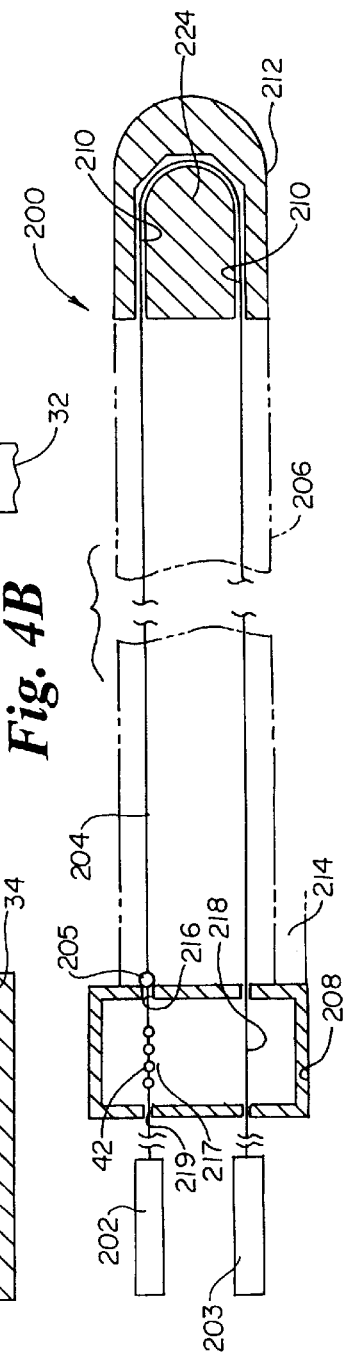

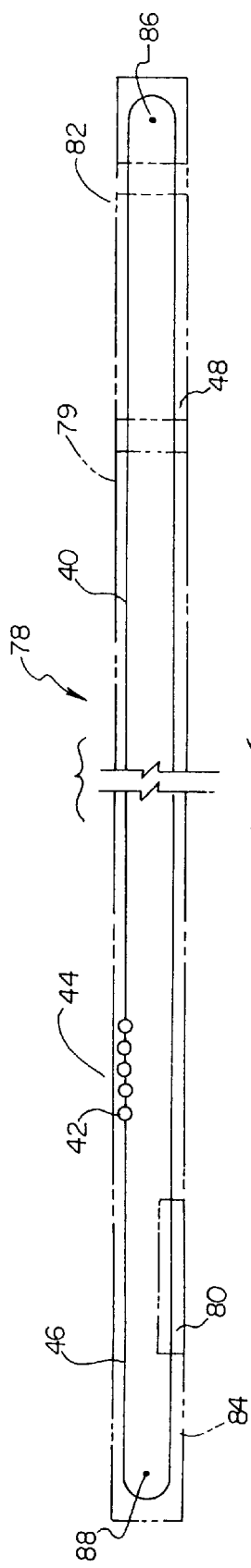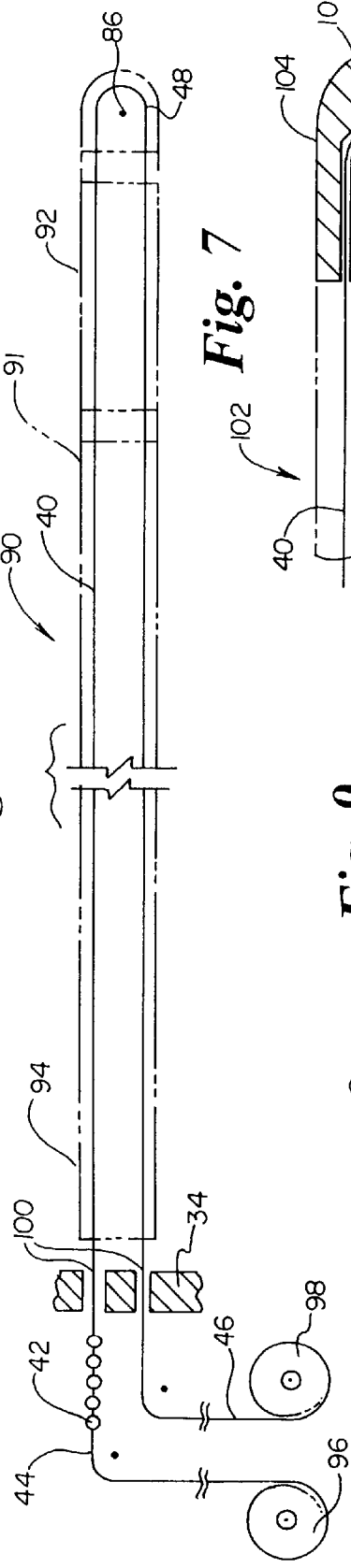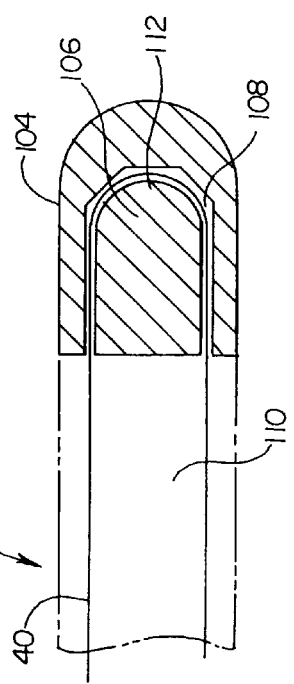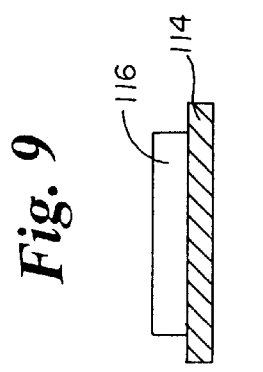

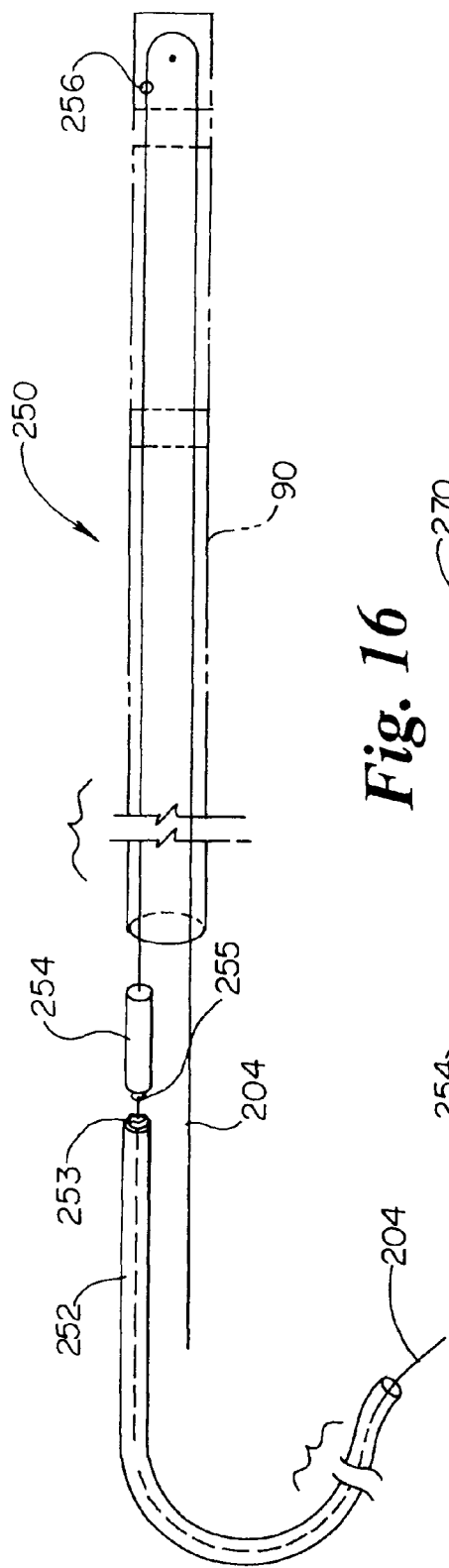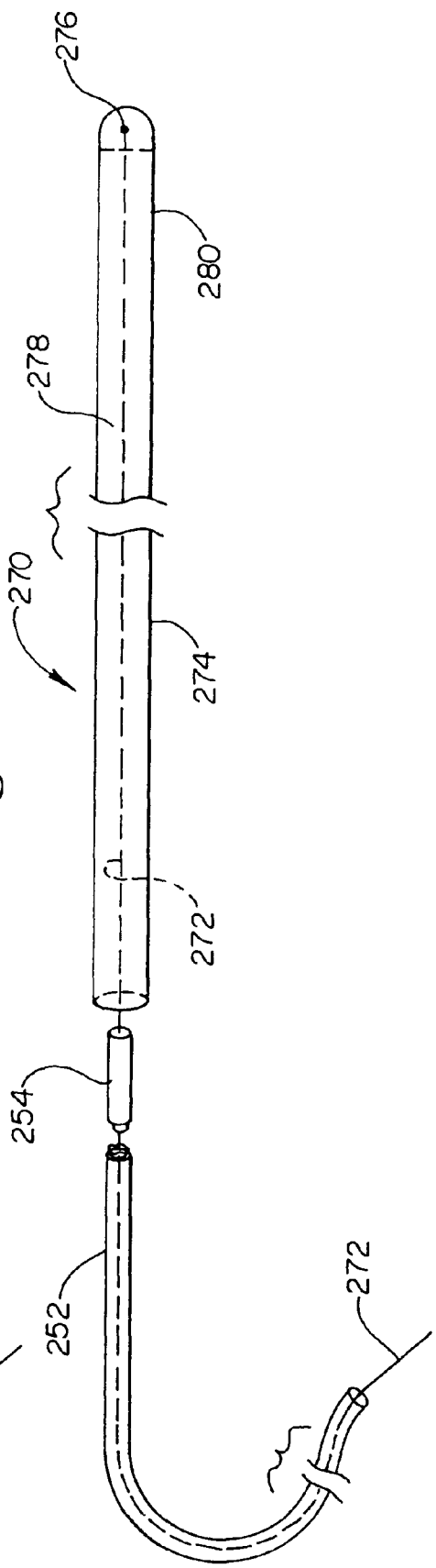

APPARATUS FOR INTRAVASCULAR RADIOACTIVE TREATMENT

FIELD OF THE INVENTION

The present invention relates generally to a method and apparatus for delivering radiation to interior sites in the human body. More specifically, the present invention relates to an intravascular catheter including a string having a radioactive section, the string being looped around a catheter distal member for advancing and retracting the radioactive string section once the catheter is positioned near a targeted site. The present invention can be used to irradiate dilated, stenosed blood vessel regions to inhibit restenosis.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve use of a guide wire and a balloon catheter, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. In approximately 30 to 50% of the cases, a restriction reappears over a period of months. The mechanism of this restenosis is not understood. The mechanism is believed to be different from the mechanism that caused the original stenosis. It is believed that rapid proliferation of vascular smooth muscle cells surrounding the dilated region may be involved. Restenosis may be in part a healing response to the dilation, including the formation of scar tissue.

Intravascular radiation, including thermal, light and radioactive radiation, has been proposed as a means to prevent or reduce the effects of restenosis. For example, U.S. Pat. No. 4,799,479 to Spears suggests that heating a dilated restriction may prevent gradual restenosis at the dilation site. In addition, U.S. Pat. No. 5,417,653 to Sahota et al. suggests that delivering relatively low energy light, following dilatation of a stenosis, may inhibit restenosis. While most clinical studies suggest that thermal radiation and light radiation are not significantly effective in reducing restenosis, some clinical studies have indicated that intravascular delivery of radioactive radiation is a promising solution to the restenosis enigma.

Delivery of radioactive radiation have been proposed as a means to prevent or reduce the effects of restenosis. For example, U.S. Pat. No. 5,199,939 to Dake et al. suggests that intravascular delivery of radiation may inhibit restenosis. Dake et al. suggest delivering radiation within the distal portion of a tubular catheter. Use of radioactive pellets, or, alternatively, liquid gas or powder, is also suggested. Fischell, in the publication EPO 0 593 136 A1, suggests placing a thin wire having a radioactive tip near the site of vessel wall trauma for a limited time to prevent restenosis.

Since radioactive radiation prevents restenosis but will not dilate a stenosis, radiation is preferably administered during or after dilatation. European Patent No. 0 688 580 to Verin discloses a device and method for simultaneously dilating a stenosis and delivering radioactive radiation. In particular, Verin '580 discloses a balloon dilatation catheter having an open-ended lumen extending therethrough for the delivery of a radioactive guide wire.

Other methods of providing radiation to treatment sites have been proposed. Thornton et al., in the PCT publication WO 96/17654 describe an inflatable treatment balloon which is inflated with a liquid containing suspended radioactive materials such as $I_{125}$ or $P_{32}$. Walker et al., in PCT publication WO 96/13303, suggest forcing radioactive capsules or pellets through a catheter using fluid pressure to arrive at the treatment site.

What would be desirable is a non-wire based, non-hydraulic, non-pneumatic device providing simple, rapid and controlled delivery and withdrawal of radiation to a treatment site within the human body. A radioactive device allowing use and re-use without sterilization would be desirable.

SUMMARY OF THE INVENTION

The present invention includes devices and methods for providing radiation to the interior of the human body. One application is the irradiation of stenosed blood vessel regions in conjunction with angioplasty to inhibit restenosis. A preferred embodiment of the device includes a string having a first region, a second region, and an intermediate region, with radioactive material within the first region. The device can further include an elongate shaft having a proximal region and a distal region, with a string return or looping member disposed in the shaft distal region. The string can be manipulated between a first position, where the radioactive string region is located near the proximal shaft region, and a second position, where the radioactive string section is located near the distal shaft portion, near the site to be treated. The string can be manipulated by pulling the string. While the string radioactive region is in the first, proximal position, the radioactive string region is preferably housed in a radiation shielding enclosure or vault. The radioactive source preferably includes Nickel-66 formed into beads which are disposed on a KEVLAR string.

In one embodiment, the string has two free ends extending through a second string aperture in the radiation vault, with the free ends being sufficiently long to allow manipulating the string between first and second positions by pulling one of the string free ends proximally. The string free ends preferably have handles attached and the vault preferably has the second string aperture suitably sized to prevent the radiation beads from exiting the vault proximally.

In one embodiment, the device has the string disposed within a single catheter lumen closed at the distal end, allowing use and re-use of a non-sterile string and radiation source within a sterile catheter. Another device includes two catheter string lumens separated at least in the distal region by a wall. The wall distal end can terminate internally, short of the catheter distal end, and can serve as the return member, allowing the string, extending distally in one lumen, to loop and return proximally through the other lumen.

The string in the present invention can be a continuous loop or a string segment having two ends, separated proximal of the radioactive region. The string can be formed of braided KEVLAR or another polymer weave or braid resistant to degradation by radioactive isotopes. The string can be manipulated by manually pulling the string through a window in the catheter proximal region. The string can be manipulated in some devices by looping the string around one or two proximally positioned pulleys. In some embodiments, the pulleys are spring biased or motor driven. Some embodiments allow for pulling only the string radioactive region into the vault, while others support pulling the catheter proximal portion into the vault, having the string radioactive region disposed within.

In an alternate embodiment of the invention, the string is disposed within a catheter having a string lumen, with the string having a stop or stop member affixed to the string distal region. The radiation source can be a radiation tube adapted to slide over the string within the string lumen. The radiation source can be advanced distally with an elongate pusher tube adapted to slide over the string within the string lumen and push the radiation tube distally until reaching the stop. One embodiment includes a distal looping member within the catheter, where the stop can be a bead, sized to engage the radiation tube distal end and affixed to the string. The radiation tube can be retracted by pulling the string, attached bead, and engaged radiation tube proximally.

Another alternate embodiment utilizes a pusher tube having a distal end adapted to secure the proximal end of the radiation tube. Threaded and snap fittings can be utilized. The pusher tube can be used to push the radiation tube distally, with the threads, snap fittings, or other securing means being engaged only to retract the radiation tube. A preferred radiation tube is a polymeric tube including radioactive beads having lumens therethrough.

In use, the device, as provided to the treating physician, can include the string radioactive region in a proximal position relative to the catheter and within the vault. The string first region extends distally, the intermediate region loops over or through the catheter distal return member, and the second region extends back proximally along the catheter. The device can be advanced within the patient to the tissue site to be irradiated. With the device distal region in place near a site, such as a recently dilated stenosis, the string radioactive region can be quickly advanced to the device distal region. After the desired exposure period, the string radioactive section can be quickly withdrawn proximally into the vault. The quick movement of the string allows for minimizing irradiation of tissue along the catheter path. The polymer string allows use of a non-wire material that can readily navigate tight turns at the catheter distal end.

BRIEF DESCRIPTION OF THE DRAWINGS

FIG. 1 is a perspective view of a radiation delivery device according to the present invention, having the radiation shielding vault drawn in phantom to illustrate a coiled catheter within;

FIG. 2 is a side, cross-sectional view of the device of FIG. 1, illustrating operation of the vault aperture door and catheter advancement out of the aperture;

FIG. 3 is a highly diagrammatic side view of a string including radioactive beads having a proximal, shielded position and a distal, irradiating position near a treatment site;

FIG. 4A is a fragmentary top, cross-sectional view of the rotation mechanism of FIG. 1, for controlling advancement and retraction of both the device and the string within the device;

FIG. 4B is a highly diagrammatic side view of a string having radioactive beads disposed within a catheter, where the string advancement and retraction is controlled with proximal handles;

FIG. 5 is a highly diagrammatic fragmentary cross-sectional side view of an embodiment of the present invention having a string access window to enable string movement by string pulling within the windows;

FIG. 6 is a highly diagrammatic fragmentary side view of an embodiment of the present invention having separate payout and takeup spools for the string;

FIG. 7 is a fragmentary longitudinal cross-sectional side view of a single lumen catheter distal end, utilizing a short, transverse, internal member as a string return member;

FIG. 8 is a transverse cross-sectional view of a radioactive bead on a string;

FIG. 9 is a longitudinal cross-sectional side view of a flat radioactive source affixed to a flat or belt shaped string;

FIG. 15 is a highly diagrammatic side view of an alternate embodiment device having a pusher tube capable of advancing a radioactive distal tube; and FIG. 16 is a highly diagrammatic side view of an alternate embodiment device having a pusher tube and coupleable radioactive distal tube.

DETAILED DESCRIPTION OF THE PREFERRED EMBODIMENTS

Figure 10:
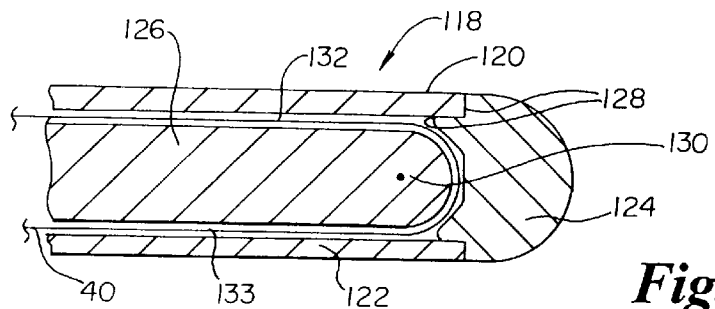
FIG. 10 is a longitudinal cross-sectional side view of the device illustrating a dual lumen embodiment distal end, utilizing a wall as a string return member.

FIG. 1 illustrates in highly diagrammatic form, a radiation delivery system 20 including a radiation shielding enclosure or vault 22 having an aperture 24. Within vault 22 is a radiation delivery elongate shaft or catheter 26, shown partially coiled about a catheter spool axis 32, having a proximal region 30 within the coil and a distal region 28 extending through vault aperture 24. A string (not show in FIG. 1) extends substantially co-extensively with shaft 26, extending distally from proximal region 30, over a return or looping member in distal region 28 (not shown in FIG. 1), and returning to proximal region 30. In a preferred embodiment, the string runs within a lumen within shaft 26. The string includes a radioactive portion, which, prior to use in treatment, is positioned near shaft proximal region 30 within vault 22. In this initial state, shaft distal region 28 may be safely and slowly advanced distally within a vessel to be treated, leaving the radioactive string portion safely within vault 22.

Referring now to FIG. 2, device 20 is shown in cross-section and from the side, with catheter or shaft 26 shown coiled about catheter spool axis 32, and having catheter distal region 28 within vault 22. Catheter distal region 28 is also shown in phantom extending through vault aperture 24, as indicated at "A". Vault 24 includes vault walls 34, vault shutter or door 36, and door housing 38. Door 36 is shown in phantom at an open position, indicated at "B". Vault walls 34 and door 36 are made of a material sufficient to block radiation emitted by the radiation source within. In a preferred embodiment, the walls and door include lead.

FIG. 3 illustrates, in a highly diagrammatic form, a string 40 having a first region 44, a second region 46, and an intermediate region 48, between first region 44 and second region 46. String 40 is shown without supporting structure such as a catheter to more clearly show one inventive concept. String first region 44 includes, as a radioactive source, beads or seeds 42. The form of the radiation source is preferably beads on a string, using a radioactive isotope such as Nickel-66. In one embodiment, the metal can be formed into spheres having central holes, threaded over the string, and compressed onto the string. However, any means of affixing the beads to the string are believed within the scope of the present invention. Preferred radiation sources include Beta and Gamma emitters, with Beta emitters being more preferred. String 40 loops around a distal string return or looping member 50 and a proximal string return member 52. In the embodiment shown, distal string return member 50 is a stationary, non rotating pin, while proximal return member 52 is a rotating pulley.

Distal string return 50 is shown disposed near a body tissue site 54 to be irradiated. String first region 44, having radioactive beads 42, is illustrated in a first position D in FIG. 3. A second, more distal position for beads 42, is shown in phantom at C. Movement between first, proximal position D and second, more distal position C, can be effected by pulling on string 40 directly, as indicated by arrows 56, or by rotating pulley 52, as indicated by arrows 58, thereby pulling string 40. The string return or looping members can be any structure suitable for looping a string over, which allows the string direction to be reversed. Preferred structures include pins, rods, pulleys, wall apertures, wall edges and wall ends.

In a radiation device, beads 42 in first position, at D, are likely to be within a radiation shielding enclosure or vault, and preferably within a catheter. In such a device, beads 42, at second position C, are preferably within a catheter distal region, outside of the vault. The radiation source can thus be moved to and from the tissue site within a catheter, as illustrated in FIG. 3.

Referring now to FIG. 4A, a top, cross-sectional view of a spooling mechanism 60 taken through catheter spool axis 32 is illustrated. Radiation delivery elongate shaft 26 is shown in the embodiment of FIG. 4A to be a catheter having a string lumen 68 containing string 40 within. Catheter 26 is shown in a distally fully extended position. Catheter 26 can be wound between spool walls 66 on a catheter spool axle 62, which can be rotated by a catheter spool knob 64. The advancement and retraction of catheter 26 through aperture 24 is controlled by the rotation of knob 64. Catheter 26, in the embodiment of FIG. 4A, includes a proximal cavity 70 containing a string spool 72 mounted on a string spool axle 74 rotatable by a string spool knob 76. Catheter 26 has axle 74 extending transversely through the proximal cavity side walls. In one embodiment, string spool 72 is included within catheter proximal cavity 70, having holes to receive string spool axle 74 therethrough. In another embodiment, the catheter terminates in a proximal port, having the string spooling mechanism external to the catheter. In such an embodiment, the string extends proximal from the catheter and can be looped around a pulley, spool, or simple string looping member.

Referring now to FIG. 4B, an alternate embodiment radiation delivery device 200 is illustrated, having a catheter 206 and a radiation vault 208. Catheter 206 has a distal region 212 and a proximal region 214, with proximal region 214 abutting radiation vault 208. A string lumen 210 extends from proximal region 214, through distal region 212, over a looping member 224, returning to proximal region 214. Vault 208 includes a radiation source lumen or cavity 217 and a string return lumen or cavity 218. In the embodiment illustrated, radiation source lumen 217 is open to, and is one in the same with, string return lumen 218. In one embodiment, the two lumens are separate. In yet another embodiment, there is no string return lumen as the string return proximal portion is not enclosed within the radiation vault. Radiation source lumen 217 includes a distal, string receiving aperture 216 and a proximal, string exiting aperture 219. In the embodiment shown, string 204 includes a stop bead 205. String receiving aperture 216 can have an inside diameter larger than the outside diameter of beads 42, yet smaller than the outside diameter of stop bead 205, allowing retraction of radioactive beads into the vault, while stopping further retraction of string 204. String exiting aperture 219 preferably has an inside diameter smaller than the outside diameter of beads 42. A pair of handles, 202 and 203, are secured to string 204, allowing advancement and retraction of radioactive beads 42. Pulling handle 203 allows advancing beads 42, and pulling handle 202 allows retracting beads 42 into vault 208. Handles 202 and 203 provide a simple apparatus for manipulating string 204 and radioactive beads 42.

Referring now to FIG. 5, a catheter 78 having a shaft 79 is illustrated, having a distal region 82, a proximal region 84 and windows 80, near the proximal region. String 40 is illustrated looping around a distal string return member 86 and a proximal string return member 88. String first region 44 having beads 42 is illustrated as advanced distally of distal region 84, while string intermediate region 48 has been advanced past catheter distal return member 86, and string second region 46 has been advanced past proximal return member 88. Windows 80 can be used to pull string 40 and move radioactive beads 42 to catheter distal region 82. Window 82 allows either hand or machine manipulation of string 40 within the window. Catheter 78 can be advanced into position, followed by string first region 44 being advanced within the catheter or shaft using window 80.

Referring now to FIG. 6, another catheter 90 having a shaft 91 is illustrated, having a distal region 92 and a proximal region 94. String 40 has first region 44, intermediate region 48, and second region 46, as in FIG. 5, but with the first and second regions not forming a loop at the catheter proximal end. A string payout spool 96 holds enough string to allow beads 42 to reach catheter distal region 92. A string takeup spool 98 has sufficient room to hold the string paid out from payout spool 96. In one embodiment, spools 96 and 98 are biased by springs such that if string 40 is released, it tends to a first position having beads 42 located proximally. In another embodiment, payout spool 96 is spring biased to return beads 42 to a proximal position, while a takeup spool 98 is motor driven. In yet another embodiment, both spools are motor driven. In still another embodiment, takeup spool 98 is located outside the vault for easy manipulation by the treating physician.

Motor driven string spools allow quick advancement and retraction of beads 42 through the catheter, minimizing exposure to tissue along the catheter path. In the embodiment shown, string 40 extends through vault wall 40 through two apertures 100, while catheter shaft 91 remains external to vault walls 34. Catheter embodiment 90 illustrates how catheter proximal region 94 can remain unshielded at all times, while string first region 44 is alternately shielded and unshielded. Catheter 91 can be inserted within the human body, while string 40, requiring no contact with the human body, need not be sterilized and can be reused, while catheter shaft 91 can be discarded after use. String 40 can be threaded through a distal string return point of another catheter prior to another use.

Referring now to FIG. 7, a single lumen catheter 102 having a distal end 104 and a single lumen 110 is illustrated. Catheter 102 utilizes a short, transverse, internal wall member 106, having a rounded wall end 112 as a string return member. In a preferred embodiment, wall member 106 is affixed at either end to the internal catheter walls, and unbound in the transverse direction, forming a string passageway 108 allowing string 40 to loop and return.

Referring now to FIG. 8, a bead 42 mounted on string 40 is illustrated in cross-section. In a preferred embodiment, string 40 is formed of braided KEVLAR, providing high string strength within a small diameter. KEVLAR braids and other polymer braids or weaves resistant to degradation by radioactive isotopes, such as Nylon, are preferred over wires. The woven strips or strings can navigate small diameter turns, such as the distal return members of the present invention. FIG. 9 illustrates an embodiment where the string has a noncircular cross section, in tape or ribbon 114, which has a flat radioactive seed or segment 116 affixed to the tape. Tape 114 can also be formed of KEVLAR or a similar material.

Referring now to FIG. 10, a catheter 118 having a shaft 120 with shaft walls 122 and an internal partition wall 126 is illustrated. The distalmost tip is not shown. Partition 126 divides catheter 118 into two string lumens 132 and 133, for containing string 40. A rounded wall end 130 to partition 126 forms a distal string return member, having string 40 looped around it. A distal tip 124 is affixed to catheter walls 122 at 128, enclosing string 40 within.

Figure 11:
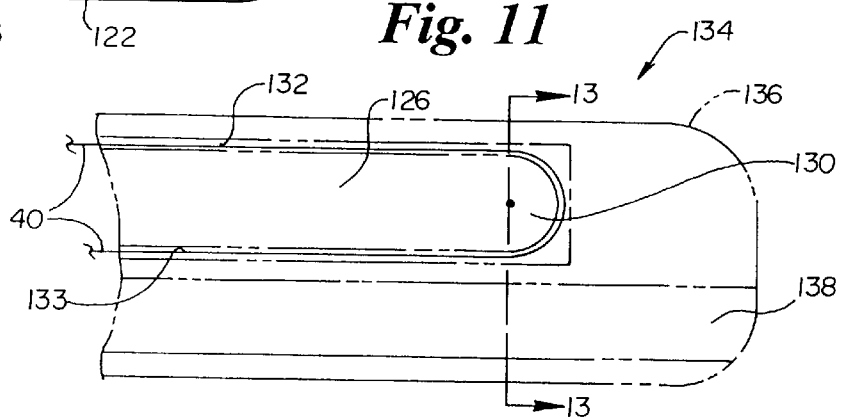
FIG. 11 is a longitudinal cross-sectional side view of an over-the-wire embodiment of the device having a distal end with two string lumens.

Referring now to FIG. 11, the distal region of an over-the-wire catheter 134 having two string lumens 132 and 133 is illustrated. Catheter 134 has a shaft 136 including an internal partition member 126 and rounded internal wall end 130, similar to the embodiment of FIG. 10. A guide wire lumen 138 extends through shaft 136, which assists in positioning the catheter distal end at a tissue site to be irradiated.

Figure 12:
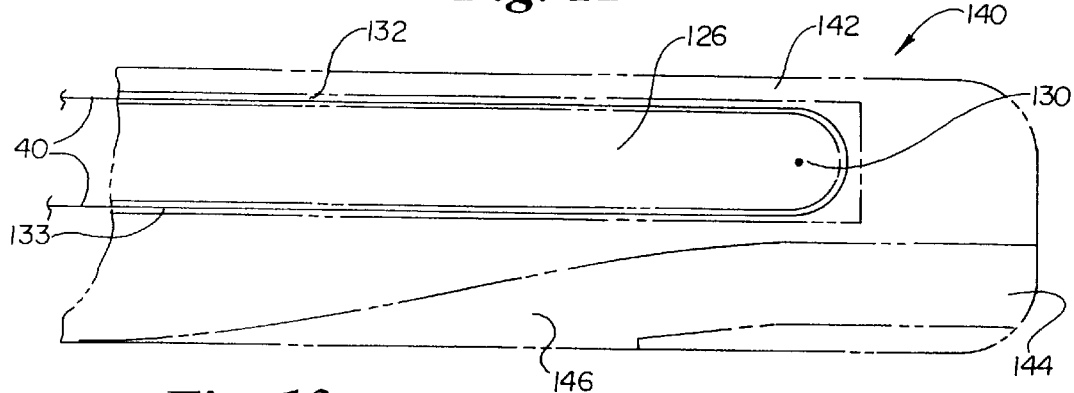
FIG. 12 is a longitudinal cross-sectional view of a single-operator-exchange embodiment of the device having a distal end with two string lumens.

Referring now to FIG. 12, the distal region of a single-operator exchange catheter 140, having a shaft 142, is illustrated. The distalmost tip portion is not shown. A short guide wire lumen 144 having a proximal port 146 is shown. Typical of single-operator-exchange catheters, guide wire lumen 144 extends a relatively short distance within the catheter distal region.

Figure 13:
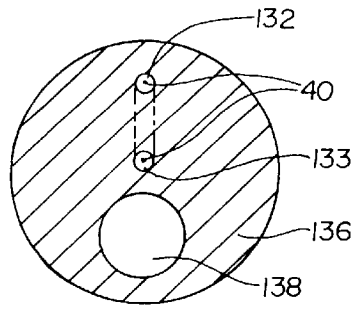
FIG. 13 is a transverse cross-sectional view of the device of FIG. 11.
Figure 14:
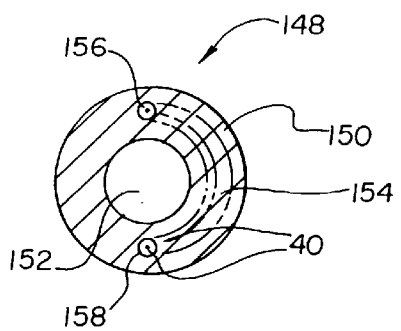
FIG. 14 is a transverse cross-sectional view of an alternate embodiment device having a single, crescent shaped string lumen and a guide wire lumen.

FIG. 13 illustrates a cross-sectional view taken through over-the-wire catheter 134 of FIG. 11. String 40 is shown running through string lumens 132 and 133. First string lumen 132 can be positioned nearer the catheter shaft surface to reduce attenuation of radiation by the shaft material, when the portion of the string carrying the radiation source is moved to the catheter distal region. FIG. 14 illustrates another embodiment catheter 14 in cross section, having a single, crescent shaped string lumen 154 with a first end portion 156, a second end portion 158 and a guide wire lumen 152. String 40 can be looped around a string return member in the catheter distal region, separating string 40 to lie distally apart near the two lumen end portions.

FIG. 15 illustrates an alternate embodiment of the invention, radiation delivery device 250, having a proximal pusher tube 252 and a distal radiation source tube 254 which can contain radioactive beads. A string 204 is threaded through both pusher tube 252 and radiation tube 254, and can contain a distal stop such as distal stop bead 256. Radiation tube 254 can serve in the preferred embodiment to space apart radioactive beads within, which are not affixed to string 204. Radiation delivery device 250 is capable of being used in conjunction with a catheter such as catheter 90, illustrated in FIG. 6. Pusher tube 252 can advance radiation tube 254 distally over string 204 until distal stop 256 is reached. Pusher tube 252 can then be retracted, leaving radiation tube 254 in place for the desired radiation exposure period.

After exposure is complete, radiation tube 254 can be retracted by providing a pusher tube that is adapted to couple with radiation tube 254. In the embodiment shown, pusher tube 252 includes a distal coupling portion 253 and radiation tube 254 includes a proximal coupling portion 255. A pusher tube can be releasable coupled with the radiation tube utilizing threaded fittings, snap fittings, or magnetic fittings. Threaded fittings can require torquing the proximal end of the pusher tube to secure and release the pusher tube from the radiation tube. Snap fittings can require applying sufficient distally directed force to the pusher tube to securably engage the radiation tube. Preferably, the snap fitting is not engaged while pushing the radiation tube distally. Radiation tube 254 can also be retracted by either pulling one end of string 204 proximally or by retracting the catheter itself proximally out of the patient. One embodiment utilizes stop 256 to retract tube 254 by pulling string 204. A preferred embodiment radiation delivery device is used on conjunction with a radiation vault or shielding enclosure.

Referring now to FIG. 16, an alternate embodiment radiation delivery device 270 including a catheter 274 having a distal region 280 and a single string lumen 278 having a string 272 disposed within. String 272 has only a single segment rather than a supply and return segment, and requires no looping member. String 272 is preferably secured to an attachment point 276 within distal region 280. Attachment point 276 can serve as the stop to prevent further distal movement of radiation tube 254. In one embodiment, pusher tube 252 is adapted to be releasably secured to distal radiation tube 254, as described with respect to FIG. 15, such that pusher tube 252 is utilized to both advance and retract radiation tube 254. In another embodiment, string 272 includes a distal stop member such as an affixed bead (not shown in FIG. 16), which is bonded to catheter distal region 280 at 276, with the bond designed to fail under tension within specified limits. In this embodiment, radiation tube 254 can be advanced with pusher tube 252 and retracted by pulling string 272 sufficiently hard to break the bond at 276, allowing the distal stop member to retract radiation tube 254 along with string 272.

The radiation delivery devices described above can be used in conjunction with, and can incorporate, suitable existing afterloader technology. In particular, motors, sensors, limit switches, timers, motor controllers, and computer controls in general can be incorporated in the invention where desired.

In use, an irradiation device including a catheter shaft having a string lumen and a distal string return member is provided. A string having a radioactive first region, a second region, and an intermediate region is threaded such that the radioactive region is positioned proximally with respect to the catheter, the intermediate region is looped distally over the string return member, and the second string region extends back proximally. In this configuration, the radioactive string portion can be located within the catheter proximal portion or extending proximally from the catheter. In either case, the radioactive string region is enclosed within a radiation shielding enclosure or vault, such that the radiation emitting portion is within the vault. In some methods, the non-radioactive portion of the string extends from the vault within a catheter prior to use, while in other methods, the entire catheter is held within the vault until use. The string threading within the catheter and disposition within the vault is preferably performed well before treatment.

A preferred use of the present invention is the irradiation of stenosed regions close to the time of angioplasty, either before, during, or after an angioplasty procedure. In embodiments utilizing a guide wire, the guide wire is advanced within the patient to the site to be treated. The shaft or catheter of the present device can then be advanced into position, such that the distal region is across the region to be irradiated. With the string catheter in place, the radiation source is still safely within the vault.

The first string region, having the radioactive beads or other radiation source, can be quickly advanced into position by pulling the second string region proximally. The string is advanced within a string lumen until it is within the catheter distal region. In one embodiment, the beads or a separate stop member on the string inhibits further distal movement past the distal region. In another embodiment having a continuous string loop, the string can be marked, to indicate at a proximal location, when the string radiation region is in proper position.

After exposure for a proper period of time, the string can be retracted through the catheter into the vault. The string can be retracted rapidly within the catheter shaft. In another embodiment, the catheter itself, with string in place, can be retracted into the vault.

The string is preferably isolated from bodily fluids, such as blood within a blood vessel, by catheter walls, allowing use and re-use of a non-sterile string within a sterile catheter. In one embodiment, the string can be sterilized and used in contact with blood, such as when the string is disposed in a lumen in contact with blood. In yet another embodiment, the string can be sterilized and disposed alongside a shaft having a distal return member such as an eyelet, the string being in contact with blood. In still another embodiment, the string can be disposed within a disposable sheath that travels along with string, allowing use and re-use of the string with different, sterile sheaths.

A preferred embodiment of the invention utilizes a catheter designed to deliver the string to the catheter distal region. One embodiment utilizes a string and vault in combination with a standard or modified catheter to deliver the string radioactive section to the site. For example, a catheter having two lumens can be used as supply and return lumens for a radioactive string. For example, a catheter having a single lumen can be used, with one string portion disposed within the lumen and a second string portion disposed outside of the shaft.

As previously stated, a preferred source of radiation for all embodiments of the present invention is the radioactive compound Nickel-66. Nickel-66 decays with a half life of 2.28 days with only low energy beta emissions and no gamma emission into its daughter element Copper-66. Copper-66 then emits high energy beta radiation with a half life of 5.10 minutes and decays into the stabile element Zinc-66. This two-step decay has a particular advantage in use in the catheters of the present invention.

The Nickel-66 acts as a carrier for the high energy copper decay allowing for time to transport the source to the end user, and also allows for disposal of the device through ordinary means in about 23 days. A Copper-66 source alone would decay quickly and not be useful without the parent Nickel. Nickel is low cost and has desirable mechanical properties in its pure form and in alloys, such as a Nickel Titanium alloy.

Another suitable radiation source is Iridium-192 encased in Nylon or other well known packaging materials. Other radiation sources include Strontium-90 and Yttrium-90 encapsulated in Silica.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. An apparatus for providing radiation within a body comprising:
    a string having a first region, a second region, an intermediate region between said first and second regions, and radioactive material affixed to said first region; and
    an elongate shaft member having a proximal region and a distal region, said distal region including means for looping said string therethrough, said string being looped over said looping means.

2. A radiation providing apparatus as recited in claim 1, wherein said elongate shaft member includes a lumen, and wherein said string is disposed in said lumen.

3. A radiation providing apparatus as recited in claim 1, further comprising means for radiation shielding having an aperture for receiving said string.

4. A radiation providing apparatus as recited in claim 3, wherein said string has
    a first position where said string radioactive first region is within said radiation shielding means and said intermediate region is looped over said looping means in said shaft distal region; and
    a second position, wherein said string radioactive first region is disposed in said shaft distal region.

5. A radiation providing apparatus as recited in claim 4, wherein said elongate shaft member includes a lumen therethrough, said string disposed in said lumen, said lumen being in communication with said looping means.

6. A radiation providing apparatus as recited in claim 5, wherein said elongate shaft has:
    an exterior in fluid communication with said body; and
    an interior isolated from fluid communication with said body, said interior including said lumen and containing said looping means such that said string is not in fluid communication with said body.

7. A radiation providing apparatus as recited in claim 6, further comprising means for advancing said string from said first position to said second position and means for retracting said string from said second position to said first position.

8. A radiation providing apparatus as recited in claim 6, further comprising a string exiting aperture in said radiation shielding means and a string lumen within said radiation shielding means in communication with said string receiving aperture and said string exiting aperture, wherein said string has two proximal ends extending from said string exiting aperture, such that said string is movable between said first and second positions by pulling one of said string proximal ends.

9. An apparatus for providing radiation within a body comprising:
    an elongate shaft member having a proximal region and a distal region, said distal region including a string return member; and a string within said shaft having a first region extending distally from said proximal region, a second region extending proximally from said distal region, an intermediate region between said first and second regions extending over said string return member, and radioactive material affixed to said first region.

10. A radiation providing apparatus as recited in claim 9, wherein said string return member is selected from the group of string looping members consisting of pins, rods, wall ends, wall edges, wall apertures, eyelets, pulleys, rollers and wheels.

11. A radiation providing apparatus as recited in claim 9, further comprising a radiation shielding enclosure having an aperture for receiving said string radioactive first region.

12. A radiation providing apparatus as recited in claim 11, wherein said elongate shaft member includes:

an exterior in fluid communication with said body;

a lumen having said string disposed within; and an interior isolated from fluid communication with said body, said interior including said lumen and said return member within, such that said string is not in fluid communication with said body.

13. A radiation providing apparatus as recited in claim 12, wherein said string has:

a first position where said string radioactive first region is within said enclosure and said intermediate region is looped over said looping means; and a second position, wherein said string radioactive first region is disposed in said distal region.

14. A radiation providing apparatus as recited in claim 13, further comprising means for advancing said string radioactive first region from said first position to said second position, and means for retracting said string radioactive first region from said second position to said first position.

15. An apparatus for providing radiation within a body comprising:

a string including a first region having a stop affixed to said first region;

an elongate tubular member having a proximal region, a distal region, and a lumen having said string disposed within, wherein said string first region is disposed within said distal region;

a radiation tube adapted to slide over said string within said tubular member lumen and adapted to be stopped by said stop; and an elongate pusher tube slidably disposed over said string within said tubular member lumen for pushing said radiation tube distally.

16. An apparatus for providing radiation within a body as recited in claim 15, wherein said stop is affixed to said string first region and not affixed to said elongate tubular member and said elongate tubular member includes a looping member within said distal region having said string looped thereover, such that said radiation tube is retractable by pulling said string and stop proximally.

17. An apparatus for providing radiation within a body as recited in claim 15, wherein said stop includes an attachment point between said string first region and said elongate tubular member distal region, wherein said pusher tube has a distal end and said radiation tube has a proximal end, wherein said pusher tube distal end is securable to said radiation tube proximal end, such that said radiation tube is retractable by advancing said pusher tube, securing said radiation tube, and retracting said radiation tube.

* * * * *